(12) United States Patent
Corzani et al.

(10) Patent No.: US 6,534,561 B1
(45) Date of Patent: *Mar. 18, 2003

(54) LOW VISCOSITY THERMOPLASTIC COMPOSITIONS FOR MOISTURE VAPOR PERMEABLE STRUCTURES AND THE UTILIZATION THEREOF IN ABSORBENT ARTICLES

(75) Inventors: Italo Corzani, Chieti (IT); Gianfranco Palumbo, Bad Homburg (DE)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/702,000

(22) PCT Filed: Jun. 1, 1999

(86) PCT No.: PCT/IB99/00997

§ 371 (c)(1),
(2), (4) Date: Dec. 6, 2000

(87) PCT Pub. No.: WO99/64077

PCT Pub. Date: Dec. 16, 1999

(30) Foreign Application Priority Data

Jun. 9, 1998 (EP) ............................................. 98110597

(51) Int. Cl.⁷ ............................................... C08L 15/00
(52) U.S. Cl. ...................................... 523/111; 523/105
(58) Field of Search ................................. 524/312, 315, 524/385, 386, 387, 389, 500; 523/105, 111

(56) References Cited

U.S. PATENT DOCUMENTS

| | | | |
|---|---|---|---|
| 4,123,410 A | | 10/1978 | Lee |
| 4,713,069 A | * | 12/1987 | Wang et al. ................. 604/378 |
| 4,854,995 A | * | 8/1989 | Kasper et al. .............. 156/243 |
| 5,424,346 A | | 6/1995 | Sinclair |
| 5,753,782 A | * | 5/1998 | Hammond et al. ......... 525/450 |
| 6,107,537 A | * | 8/2000 | Elder et al. ................. 604/364 |
| 6,133,400 A | * | 10/2000 | Helmke ....................... 528/83 |

FOREIGN PATENT DOCUMENTS

| | | |
|---|---|---|
| GB | 0 085 182 | 11/1997 |
| GB | 0 806 283 | 11/1997 |

* cited by examiner

*Primary Examiner*—Edward J. Cain
*Assistant Examiner*—Katarzyna Wyrozebski-Lee

(57) ABSTRACT

The present invention relates to thermoplastic compositions for making a liquid impermeable moisture vapor permeable layer by coating the composition onto a substrate. The thermoplastic compositions comprise preferred thermoplastic polymers and suitable hydrophilic plasticisers to adjust the viscosity of the composition at the process conditions. The layers made from the thermoplastic compositions of the present invention can find a variety of applications wherein moisture vapour permeability is desirable, such as within absorbent articles for example diapers, sanitary napkins, panty liners and incontinence products, and also protective bedding covers, protective clothing and the like.

12 Claims, No Drawings

LOW VISCOSITY THERMOPLASTIC COMPOSITIONS FOR MOISTURE VAPOR PERMEABLE STRUCTURES AND THE UTILIZATION THEREOF IN ABSORBENT ARTICLES

FIELD OF THE INVENTION

The present invention relates to thermoplastic compositions for making a moisture vapour permeable, liquid impermeable layer by coating the composition onto a substrate. The compositions of the present invention can find a variety of applications, wherein moisture vapour permeability is desirable for example within absorbent articles such as diapers, sanitary napkins, panty liners and incontinence products, protective bedding covers, protective clothing and the like.

BACKGROUND OF THE INVENTION

Thermoplastic films which provide a liquid barrier in addition to providing moisture vapour permeability are known in the art. Particularly preferred are hydrophilic continuous films that do not allow the flow of moisture vapour through open pores or apertures in the material, but do transfer substantial amounts of moisture vapour through the film by absorbing water on one side of the film where the moisture vapour concentration is higher, and desorbing or evaporating it on the opposite side of the film where the moisture vapour concentration is lower.

For example WO 95/16746 discloses films prepared from mixtures of a) block copolyether ester, block copolyether amides (e.g. Pebax™) and or polyurethane and b) thermoplastic polymer which is incompatible with a, and c) a compatibiliser. The films are liquid impermeable and have moisture vapour permeability of about 700 g/m$^2$·day. Also, U.S. Pat. No. 5,447,783 discloses a vapour permeable water resistant multi component film structure having at least three layers. The outer layers are hydrophobic copolyetherester elastomers having a thickness of 1.3–7.6 micrometers and a WVTR of 400–2500 g/m$^2$·24h and the inner layer is a hydrophilic copolyetherester elastomer having a thickness of 7.6–152 micrometers and a WVTR of at least 3500 g/m$^2$·24h.

U.S. Pat. No. 5,445,875 discloses a waterproof, bloodproof and virusproof breathable laminate. The laminate comprises a woven/nonwoven fabric and an extruded film such as Hytrel™ having a thickness of about 1 mil (25.4 micrometers).

Other composite laminates are described for example in U.S. Pat. No. 5,599,610 which discloses tri-laminated fabric for surgical gowns comprising outer layers of woven fabric and an inner layer of a microporous polyurethane membrane. The microporous film has a thickness of 12–55 micrometers and a MVTR of 1100 g/m$^2$·24h upright and 5500 g/m$^2$·24h inverted (ASTM E96-B). Polyether-polyurethane adhesive is used to join the layers.

Similarly, U.S. Pat. No. 5,532,053 discloses a high moisture transmission medical film which can be laminated onto a nonwoven material. The laminate film comprises a first layer of polyetherester copolymer and second and third layers selected from a specified group of polymers. The film has a MVTR of greater than 750 g/m$^2$·24h (ASTM F1249) and a thickness of less than 1 mil (25.4micrometer) preferably 0.6 mil to 0.75 mil (15–19 micrometers).

U.S. Pat. No. 4,938,752 discloses absorbent articles comprising films of copolyether esters which have reduced water permeability, a water vapour permeability of 500 g/m$^2$·24h (as measured in a specified described test) and a thickness of 5–35 micrometers. There is no disclosure of a supportive substrate.

U.S. Pat. No. 4,493,870 discloses a flexible layered waterproof product comprising a textile material covered with a film of a copolyetherester having an MVTR of at least 1000 g/m$^2$·24h (ASTM E96-66) having a thickness of 5 to 35 micrometers.

GB 2024100 discloses a flexible layered water resistant article comprising a microporous hydrophobic outer layer which is moisture vapour permeable but resist liquids and a hydrophilic inner layer of polyetherpolyurethane having a MVTR of above 1000 g/m$^2$·24h.

Compositions known for providing hydrophilic continuous moisture vapour permeable, liquid impermeable films or layers include thermoplastic polymers such as polyurethanes, poly-ether-amides block copolymers, polyethylene-acrylic acid copolymers, polyethylene oxide and its copolymers, poly lactide and copolymers, polyamides, polyester block copolymers, sulfonated polyesters, poly-ether-ester block copolymers, poly-ether-ester-amide block copolymers, polyacrylates, polyacrylic acids and derivatives, ionomers, polyethylene-vinyl acetate with a vinyl acetate content of more than 28% by weight, polyvinyl alcohol and its copolymers, polyvinyl ethers and their copolymers, poly-2-ethyl-oxazoline and derivatives, polyvinyl pyrrolidone and its copolymers, thermoplastic cellulose derivatives, or mixtures thereof. Such compositions can be used for making layers and films featuring high values of moisture vapour permeability while being liquid impermeable, which therefore are particularly preferred for incorporation in disposable absorbent articles.

However, a problem associated with films and layers made from the above mentioned thermoplastic compositions is that such compositions are typically highly viscous in the plastic state at the process conditions, and are processable only by means of extrusion techniques. Extrusion processes for making films and layers from thermoplastic polymers are well known, but have the disadvantage of being rather complex; they in fact require expensive equipment, typically comprising a high power screw extruder to force the material in the plastic state through a slit die to form the film or layer. Extrusion process conditions also typically involve rather high temperatures and pressures. Moreover an extrusion apparatus for the formation of a film or layer cannot be easily incorporated into a production line, e.g. of disposable absorbent products. Extrusion processes moreover are not suitable for the production of films having a particularly low thickness, e.g. in the range of 5–10 μm.

Furthermore, in case of laminated composite structures, in which i.e. a layer of the preferred moisture vapour permeable, liquid impermeable composition is laminated to a substrate, e.g. a fibrous layer, the addition of an adhesive in order to ensure permanent fixation of the film onto the substrate is often required. However, this in turn detrimentally affects the overall moisture vapour permeability of the resulting composite, and adds complexity to the production process.

Hence, there is a need to provide compositions for making a hydrophilic continuous moisture vapour permeable, liquid impermeable layer having preferred characteristics of moisture vapour permeability and liquid imperviousness which are also readily processable so as to provide a preferably thin film coating onto a substrate, so avoiding the need of complex traditional extrusion apparatuses.

SUMMARY OF THE INVENTION

The present invention relates to a thermoplastic composition comprising:

- a thermoplastic polymer or mixture of polymers having a viscosity higher than 5000 poise at a temperature of 20° C. above the DSC melting point of the polymer or mixture of polymers, evaluated as described in the text, and at a frequency of 1 rad/sec, the thermoplastic polymers being selected from the group consisting of polyurethanes, poly-ether-amides block copolymers, polyethylene-acrylic acid copolymers, polyethylene oxide and its copolymers, poly lactide and copolymers, polyamides, polyester block copolymers, sulfonated polyesters, poly-ether-ester block copolymers, poly-ether-ester-amide block copolymers, polyacrylates, polyacrylic acids and derivatives, ionomers, polyethylene-vinyl acetate with a vinyl acetate content of more than 28% by weight, polyvinyl alcohol and its copolymers, polyvinyl ethers and their copolymers, poly-2-ethyl-oxazoline and derivatives, polyvinyl pyrrolidone and its copolymers, thermoplastic cellulose derivatives, or mixtures thereof,
- a suitable compatible plasticiser or blend of plasticisers for adjusting said viscosity,
- wherein said thermoplastic composition has a viscosity of from 50 poise to 4000 poise at a frequency of 1 rad/s at a temperature of 210° C. or less and a viscosity of less than 2000 poise at a frequency of 1000 rad/s at a temperature of 210° C. or less.

DETAILED DESCRIPTION OF THE INVENTION

Preferred thermoplastic polymers for providing hydrophilic continuous moisture vapour permeable, liquid impermeable films or layers are polyurethanes, poly-ether-amides block copolymers, polyethylene-acrylic acid copolymers, polyethylene oxide and its copolymers, poly lactide and copolymers, polyamides, polyester block copolymers, sulfonated polyesters, poly-ether-ester block copolymers, poly-ether-ester-amide block copolymers, polyacrylates, polyacrylic acids and derivatives, ionomers, polyethylene-vinyl acetate with a vinyl acetate content of more than 28% by weight, polyvinyl alcohol and its copolymers, polyvinyl ethers and their copolymers, poly-2-ethyl-oxazoline and derivatives, polyvinyl pyrrolidone and its copolymers, thermoplastic cellulose derivatives, and mixtures thereof. Among the above mentioned thermoplastic polymers particularly preferred are thermoplastic poly-ether-amide block copolymers (e.g. Pebax™), thermoplastic poly-ether-ester-amide block copolymers, thermoplastic polyester block copolymers (e.g. Hytrel™), thermoplastic polyurethanes (e.g. Estane™), or mixtures thereof. Such thermoplastic polymers or mixture of polymers are typically highly viscous in the melted state at the process conditions that are typical of the known processes of film or layer formation, e.g. an extrusion process involving a high power screw extruder. Specifically the thermoplastic polymer or mixture of polymers typically have a viscosity higher than 5000 poise at a temperature of 20° C. above the DSC (Differential Scanning Calorimetry) melting point, which is the temperature identified as that corresponding to the DSC peak, or corresponding to the highest DSC peak in case of a mixture of polymers showing more than one peak, and at a frequency of 1 rad/sec.

The viscosity of the thermoplastic compositions of the present invention is adjusted by providing the thermoplastic composition comprising the thermoplastic polymer or mixture of polymers with a suitable plasticiser, or blend of plasticisers, that is compatible with the thermoplastic polymers and that lowers the viscosity of the thermoplastic composition in the melted state.

According to the present invention the thermoplastic compositions have the following complex viscosities ($\eta^*$):

50 poise $<\eta^*<$4000 poise, preferably 100 poise $<\eta^*<$2000 poise, more preferably 100 poise $<\eta^*<$1000 poise, at a frequency of 1 rad/s at a temperature of 210° C. or less and $\eta^*<$2000 pose, preferably $\eta^*<$1000 poise, more preferably $\eta^*<$500 poise at a frequency of 1000 rad/s at a process temperature (T) of 210° C. or less, wherein $\eta^*$ represents the complex viscosity of the thermoplastic polymeric composition. Preferably the temperature T is 200° C. or less and more preferably 180° C. or less and most preferably from 200° C. to 50° C.

It has been surprisingly found that thermoplastic compositions having the complex viscosity described allow for a film or layer to be coated onto a substrate using typical coating conditions and apparatuses known in the art for the coating of low viscosities hot melt compositions in a layer having a required thickness onto a substrate, while keeping the advantageous characteristics of the preferred thermoplastic polymers in providing hydrophilic continuous moisture vapour permeable, liquid impermeable layers or films.

It has also been found that thermoplastic compositions having such viscosities can provide very thin films or layers.

Suitable plasticisers for use in the thermoplastic compositions according to the present invention include citric acid esters, tartaric acid esters, glycerol and its esters, adipates, sebacates, sorbitol, epoxidized vegetal oils, polymerised vegetal oils, polyols, phthalates, liquid polyesters, glycolates, p-toluene sulfonamide and derivatives, glycols and polyglycols, sorbitan esters, phosphates, monocarboxylic fatty acids ($C_8$–$C_{22}$) and their derivatives, and mixtures thereof.

Preferably the thermoplastic composition of the present invention comprises from 10% to 80%, more preferably from 25% to 70% by weight of the thermoplastic composition, of the thermoplastic polymer or mixture of polymers, and from 20% to 90%, preferably from 30% to 75% by weight of the thermoplastic composition, of the suitable plasticiser or blend of plasticisers.

The thermoplastic compositions of the present invention may in addition comprise additional optional components to further improve the processability of the compositions and also the mechanical characteristics as well as other characteristics as tackiness, resistance to ageing by light and oxygen, visual appearance etc., of the films or layers formed from such thermoplastic compositions.

Such optional components include tackifying resins or blends of tackifying resins having a softening point of 125° C. or less. Preferred resins, which may be present by up to 50% by weight of the thermoplastic composition, may be selected from rosins and rosin esters, hydrocarbon resins, aliphatic resins, terpene and terpene-phenolic resins, aromatic resins, synthetic $C_5$ resins, mixtures of synthetic $C_5$–$C_9$ resins, and mixtures thereof. Other optional components of said thermoplastic compositions include antioxidants, anti-ultraviolets, pigments and mixtures thereof, which may be present within the composition at a level of up to 10% by weight of the composition.

A thermoplastic composition according to the present invention can be manufactured with a process that will typically comprise the steps of providing the thermoplastic polymer or mixture of polymers and the suitable plasticiser or blend of plasticisers, heating the components and compounding them, e.g. with a known suitable mixer to form the thermoplastic composition in the molten state having the desired complex viscosity η*.

According to the present invention a moisture vapour permeable, liquid impervious layer can be formed from the thermoplastic composition of the present invention by coating said thermoplastic composition onto a substrate. The films or layers formed from the thermoplastic compositions of the present invention preferably have a moisture vapour transport rate of at least 100 g/m²·24h, preferably at least 300 g/m²·24h, most preferably at least 500 g/m²·24h, with a thickness of at least 0.5 μm.

A process for making a layer or film from a thermoplastic composition according to the present invention typically comprises the steps of providing said composition, heating it to make it flowable, and coating said composition in the molten state onto a substrate in a layer having the desired thickness. While said substrate can be simply a formation substrate, onto which the thermoplastic composition is coated in order to form a film or layer of the desired thickness which is subsequently separated from said substrate and used as such, in an embodiment of the present invention a moisture vapour permeable, water impervious composite can also be formed which comprises the thermoplastic composition and a substrate onto which said thermoplastic composition is coated, wherein the substrate is also preferably moisture vapour permeable.

Such embodiment of the present invention provides a moisture vapour permeable, liquid impervious composite wherein the contribution of the layer formed from the thermoplastic composition of the present invention to the performance of the composite material resides only in the provision of a liquid barrier and hence could be advantageously provided as thinly as possible. The remaining performance physical criterion being preferably provided by the provided substrate, that therefore preferably acts also as a support layer.

The substrate, or support layer may be any useful layer which is preferably also moisture vapour permeable, preferably having a moisture vapour permeability of at least 100 g/m²·24h, more preferably at least 300 g/m²·24h, and most preferably at least 500 g/m²·24h.

Suitable substrates for use herein as support layers include two dimensional, planar micro and macro-porous films; macroscopically expanded films; formed apertured films; nonwoven and woven layers. According to the present invention the apertures in said layer may be of any configuration, but are preferably spherical or oblong and may also be of varying dimensions. The apertures preferably are evenly distributed across the entire surface of the layer, however layers having only certain regions of the surface having apertures are also envisioned.

Suitable two dimensional porous planar layers of the backsheet may be made of any material known in the art, but are preferably manufactured from commonly available polymeric materials. Suitable materials are for example Goretex™ or Sympatex™ type materials well known in the art for their application in so-called breathable clothing. Other suitable materials include XMP-1001 of Minnesota Mining and Manufacturing Company, St. Paul, Minn., USA and Exxaire XBF-101W, supplied by the Exxon Chemical Company. As used herein the term two dimensional planar layer refers to layers having a depth of less than 1 mm, preferably less than 0.5 mm, wherein the apertures have an average uniform diameter along their length and which do not protrude out of the plane of the layer. The apertured materials for use as a backsheet in the present invention may be produced using any of the methods known in the art such as described in EPO 293 482 and the references therein. In addition the dimensions of the apertures produced by this method may be increased by applying a force across the plane of the backsheet layer (i.e. stretching the layer).

Suitable apertured formed films include films which have discrete apertures which extend beyond the horizontal plane of the garment facing surface of the layer towards the core thereby forming protuberances. The protuberances have an orifice located at its terminating end. Preferably said protuberances are of a funnel shape, similar to those described in U.S. Pat. No. 3,929,135. The apertures located within the plane and the orifices located at the terminating end of protuberance themselves maybe circular or non circular provided the cross sectional dimension or area of the orifice at the termination of the protuberance is smaller than the cross sectional dimension or area of the aperture located within the garment facing surface of the layer. Preferably said apertured performed films are uni directional such that they have at least substantially, if not complete one directional fluid transport towards the core.

Suitable macroscopically expanded films for use herein include films as described in for example in U.S. Pat. No. 4,637,819 and U.S. Pat. No. 4,591,523.

Preferred support layers for use herein include woven and nonwoven layers, most preferably hydrophobic fibrous layers such as hydrophobic nonwoven.

The composites of this preferred embodiment of the present invention are particularly advantageous as they allow the possibility of providing a composite wherein the thermoplastic composition may be coated onto the support substrate as a layer with the desired thickness. Typical coating conditions and apparatuses known in the art for the direct coating of low viscosities hot melts can be readily utilised in order to provide the thermoplastic composition at the desired thickness.

A possible method for forming a composite laminate by coating the thermoplastic composition onto a substrate acting as a support layer is described in PCT application WO 96/25902.

At least at the coating temperature, the thermoplastic composition in form of a layer preferably exhibits adhesive properties on the supportive substrate in order to form the preferred composite such that no additional adhesive is required to achieve a permanent attachment between the thermoplastic composition and the substrate. In some applications it may be also desirable that the thermoplastic composition remains tacky at any temperature i.e. it is formulated so to have the typical characteristics of a pressure sensitive adhesive.

The thermoplastic compositions of the present invention and the moisture vapour permeable, liquid impervious layers and composites formed therefrom find utility in a number of applications wherein liquid imperviousness and moisture vapour permeability are desirable. In particular the present invention can be effectively utilised within absorbent articles such as diapers, sanitary napkins, panty liners and incontinence products; perspiration pads such as underarm-, wrist- and head perspiration pads, collar inserts, shoe inserts, hat bands and breast pads; protective bedding covers, protective clothing and the like. Preferably the moisture vapour permeable, liquid impervious layers and composites formed from the thermoplastic compositions of the present invention have a moisture vapour transfer rate of at least 100 g/m²·24h, more preferably at least 300 g/m²·24h, and most preferably at least 500 g/m²·24h.

A moisture vapour permeable, liquid impervious composite structure formed by coating the thermoplastic composition of the present invention onto a suitable substrate finds particular utility as the backsheet for absorbent articles especially sanitary napkins and panty liners. Such articles will typically comprise components known to the skilled person such as a liquid pervious topsheet, an absorbent core and backsheet and may optionally comprise fastening means, wings, and the like.

EXAMPLE

A polyether-amide block copolymer available from Elf Atochem (France) commercialised under the trade name Pebax MV 1074 was compounded with Triethyl Citrate available from Aldrich Co. and Irganox 1010 (anti oxidant agent) available from Ciba-Geigy.

The polymer has a DSC peak melting point of 158° C. and at 178° C. and at the frquency of 1 rad/s shows a complex viscosity of 6410 Poise.

The final formulation in percent by weight had the following composition:

| | |
|---|---|
| 30% | Pebax MV 1074 |
| 69% | Triethyl Citrate |
| 1% | Irganox 1010 |

The blend was melt extruded at 160° C. to obtain a film having a thickness equal to 5 µm. At the extruding temperature it was found to have complex viscosities of 517 poise and 172 Poise respectively at 1 and 1000 rad/s shear rate. The film was then laminated directly onto a substrate constituted by a carded hydrophobic 100% polypropylene nonwoven 34 g/m² (support layer) commercialised under the trade name Sawabond 4326, available form Sandler (Germany). The composite substrate had a moisture vapour transfer rate of 2530 g/m²·24hrs.

According to the present invention the complex viscosity is measured using a Rheometer RDA-II available from Rheometrics Co. Water vapour permeability is measured at 23° C. according to the ASTM E-96 "Upright Cup" method.

What is claimed is:

1. A continuous film or layer formed from a thermoplastic composition comprising:
    a thermoplastic polymer or mixture of polymers having a viscosity higher than 5000 poise at a temperature of 20° C. above the DSC melting point of said polymer or mixture of said polymers and at a frequency of 1 rad/sec, said thermoplastic polymers selected from the group consisting of polyurethanes, poly-ether-amides block copolymers, polyethylene-acrylic acid copolymers, polyethylene oxide and its copolymers, poly lactide and copolymers, polyamides, polyester block copolymers, sulfonated polyesters, poly-ether-ester block copolymers, poly-ether-ester-amide block copolymers, polyacrylates, polyacrylic acids, ionomers, polyethylene-vinyl acetate with a vinyl acetate content of more than 28 weight %, polyvinyl alcohol and its copolymers, polyvinyl ethers and their copolymers, poly-2-ethyl-oxazoline, polyvinyl pyrrolidone and its copolymers, and mixtures thereof,
    a suitable compatible hydrophilic plasticiser or blend of hydrophilic plasticisers,
    wherein said thermoplastic composition has a viscosity of from 50 poise to 4000 poise at a frequency of 1 rad/s at a temperature of 210° C. or less and a viscosity of less than 2000 poise at a frequency of 1000 rad/s at a temperature of 210° C. or less,
    wherein said compatible hydrophilic plasticisers are selected from the group consisting of acids, esters, amides, alcohols, polyalcohols, and mixtures thereof,
    and wherein said continuous film or layer is liquid impervious and has a water vapour transmission rate of at least 300 g/m²·24h, said water vapour transmission rate measured at 23° C. according to the ASTM E-96 "Upright Cup" method.

2. A thermoplastic composition according to claim 1, wherein said thermoplastic polymer comprises thermoplastic poly-ether-amide block copolymers, thermoplastic poly-ether-ester-amide block copolymers, thermoplastic polyester block copolymers, thermoplastic polyurethanes, or mixtures thereof.

3. A thermoplastic composition according to claim 1, wherein said composition comprises:
    from 10% to 80% by weight of said thermoplastic composition, of said polymer or mixture of polymers,
    from 20% to 90% by weight of said thermoplastic composition, of said plasticiser or blend of plasticisers,
    from 0 to 50% by weight of a suitable compatible tackifyer resin.

4. A thermoplastic composition according to claim 1, wherein said composition comprises:
    from 25% to 70% by weight of said thermoplastic composition, of said polymer or mixture of polymers,
    from 30% to 75% by weight of said thermoplastic composition, of said plasticiser or blend of plasticisers,
    from 0% to 50% by weight of a suitable compatible tackifyer resin.

5. A thermoplastic composition according to claim 1, wherein said plasticisers are selected from citric acid esters, tartaric acid esters, glycerol and its esters, adipates, sebacates, sorbitol, epoxidized vegetal oils, polymerised vegetal oils, polyols, phthalates, liquid polyesters, glycolates, p-toluene sulfonamide and derivatives, glycols and polyglycols, sorbitan esters, phosphates, monocarboxylic fatty acids ($C_8$–$C_{22}$) and their derivatives, and mixtures thereof.

6. A thermoplastic composition according to claim 1, wherein said tackifier resins are selected from rosins and rosin esters, hydrocarbon resins, aliphatic resins, terpene and terpene-phenolic resins, aromatic resins, synthetic $C_5$ resins, mixtures of synthetic $C_5$–$C_9$ resins, and mixtures thereof.

7. A moisture vapour permeable layer formed from the thermoplastic composition of claim 1, wherein said layer is liquid impervious and has a water vapour transmission rate (WVTR) of at least 300 g/m²·24h with a thickness of said layer of at least 0.5 µm.

8. A moisture vapour permeable, liquid impervious composite comprising the layer of claim 7, coated onto a substrate, said substrate being moisture vapour permeable.

9. An absorbent article comprising a moisture vapour permeable, liquid impervious layer according to claim 7.

10. An absorbent article comprising a moisture vapour permeable, liquid impervious composite according to claim 9.

11. A process for making a thermoplastic composition according to claim 1 comprising the steps of:
    providing said thermoplastic polymer or mixture of polymers, providing said suitable plasticiser or blend of plasticisers, heating said thermoplastic polymer or mixture of polymers and said plasticiser or blend of plasticisers and compounding them to form said thermoplastic composition in the molten state.

12. A process for making a layer from the thermoplastic composition of claim 1, comprising the steps of:

providing said thermoplastic composition, heating said thermoplastic composition to make it flowable, coating said thermoplastic composition onto a substrate in a layer having a desired thickness.

* * * * *

UNITED STATES PATENT AND TRADEMARK OFFICE
CERTIFICATE OF CORRECTION

PATENT NO.     : 6,534,561 B1
DATED          : March 18, 2003
INVENTOR(S)    : Italo Corzani et al.

It is certified that error appears in the above-identified patent and that said Letters Patent is hereby corrected as shown below:

<u>Column 8,</u>
Line 63, delete "9" and insert -- 8 --.

Signed and Sealed this

Fifteenth Day of June, 2004

JON W. DUDAS
*Acting Director of the United States Patent and Trademark Office*